(12) United States Patent
Prabhu et al.

(10) Patent No.: US 6,306,077 B1
(45) Date of Patent: Oct. 23, 2001

(54) MANAGEMENT OF PHYSIOLOGICAL AND PSYCHOLOGICAL STATE OF AN INDIVIDUAL USING IMAGES OVERALL SYSTEM

(75) Inventors: Girish V. Prabhu, Fairport; Cecelia M. Horwitz, Penfield; Paige Miller, Rochester; Richard N. Blazey, Penfield; Elena A. Fedorovskaya, Pittsford; Swatee N. Surve, Rochester; David L. Patton, Webster; Laurie Schaefer, Canandaigua; John R. Fredlund; Jose V. Mir, both of Rochester, all of NY (US); Peter A. Parks, Topeka, KS (US)

(73) Assignee: Eastman Kodak Company, Rochester, NY (US)

( * ) Notice: Subject to any disclaimer, the term of this patent is extended or adjusted under 35 U.S.C. 154(b) by 0 days.

(21) Appl. No.: 09/430,580

(22) Filed: Oct. 29, 1999

Related U.S. Application Data

(63) Continuation of application No. 09/031,245, filed on Feb. 26, 1998, now Pat. No. 6,102,846.

(51) Int. Cl.[7] .................................................. A61M 21/00
(52) U.S. Cl. ............................... 600/26; 600/27; 128/898
(58) Field of Search ................................... 434/236, 237, 434/238; 128/898; 600/26, 27

(56) References Cited

U.S. PATENT DOCUMENTS

| | | |
|---|---|---|
| 3,855,998 | 12/1974 | Hidalgo-Briceno . |
| 4,632,126 | 12/1986 | Aguilar . |
| 5,047,930 | 9/1991 | Martens et al. . |
| 5,253,168 | 10/1993 | Berg . |
| 5,304,112 | 4/1994 | Mrklas et al. . |
| 5,343,871 | 9/1994 | Bittman et al. . |
| 5,465,729 | 11/1995 | Bittman et al. . |
| 5,596,994 | 1/1997 | Bro . |
| 5,676,138 | 10/1997 | Zawilinski . |

OTHER PUBLICATIONS

Affective judgement and psychophysiological response: dimensional covariation in the evaluation of pictorial stimuli; by: Greenwald, Cook and Lang; Journal of Pyschophysiology 3 (1989), pp. 51–64.

Remembering Pictures: Pleasures and Arousal in Memory, by: Bradley, Greenwald, Petry and Lang; Hournal of Experimental Psychology, Learning Memory and Cognition; 1992, vol. 18, No. 2, pp. 379–390.

Looking at Pictures: Affective, facial, visceral, and behavioral reactions; by: Lang, Greenwald, Bradley, and Hamm, Psychophysiology, 30 (1993), pp. 261–273.

Picture media and emotion: Effects of a sustained affective context; by: Bradley, Cuthbert, and Lang, Psychophysiology, 33 (1996), pp. 662–670.

Emotional arousal and activation of the visual cortex: An fMRI analysis; by: Lang, Bradley, Fitzsimmons, Cuthbert, Scott, Bradley, Moulder, and Nangia; Psychophysiology, 25 (1998), pp. 199–210.

*Primary Examiner*—Linda C. M. Dvorak
*Assistant Examiner*—R. Kearney
(74) *Attorney, Agent, or Firm*—William F. Noval

(57) ABSTRACT

A method of managing a physiological or psychological state of an individual using images comprising: determining an individual's direction or preference for a state management session; based on the determination, deciding whether a current set of images selected through a personal image profile session, will achieve the desired management effect; if the current set are deemed satisfactory, presenting the set of images to the individual to achieve management of the individual's state.

5 Claims, 10 Drawing Sheets

MANAGEMENT OF PHYSIOLOGICAL AND PSYCHOLOGICAL STATE OF AN INDIVIDUAL USING IMAGES OVERALL SYSTEM

CROSS REFERENCE TO RELATED APPLICATIONS

This application is a continuation under 35 U.S.C. sec. 120 of the earlier filing date of U.S. patent application Ser. No. 09/031,245, filed Feb. 26, 1998, U.S. Pat. No. 6,102,846 inventors Patton et al., for A SYSTEM AND METHOD OF MANAGING A PSYCHOLOGICAL STATE OF AN INDIVIDUAL USING IMAGES.

FIELD OF THE INVENTION

This invention relates in general to the management of a physiological and/or psychological state of an individual and more particularly to the management of the physiological and/or psychological state of an individual through the use of images which have been customized for use by the individual and which can be part of a self-help process.

BACKGROUND OF THE INVENTION

The physical, emotional and mental well-being of an individual can contribute greatly to the quality of life of that individual. In our hyperactive, hyperkinetic world, stress results in numerous physical reactions, such as, headache, muscle tension, dizziness or sleeplessness, weight gain, chronic coughing, nervous ticks, stomach upset and shortness of breath. Job stress alone is estimated to cost American business $300,000,000,000 annually. Stress is the response of the body and/or mind to a demand placed upon it. Stress can be caused by major events in one's life, such as, death of a loved one, marital breakup, personal injury or sickness, and job loss. Stress can also result from our day-to-day hectic style of living, where one attempts to excel simultaneously at being a super employee, a super parent, a super spouse, and a super citizen. Unless chronic stress is controlled, one puts oneself at risk for a host of serious problems, such as, heart disease, stroke, migraines, muscle and nerve disorders.

The typical path to obtain relief from stress is to visit one's doctor. Stress conditions result in up to 70% of all doctor's visits. Typically, drugs are prescribed to relieve stress. One stress reducing medication alone accounts for $6,000,000 per day in sales. Thus, alternative approaches to traditional medicine have become increasingly popular. Resort to Eastern religions, transcendental meditation, and biofeedback techniques have been proposed to empower the individual to reduce stress without the potential deleterious effects of powerful and expensive prescription drugs or invasive surgery.

It has been proposed to use images for the purpose of optimizing one's physiological and psychological state. There are several reasons for this.

(1) It has been shown that one can measure a reliable physiological response for images that differ in valence and arousal. It has been demonstrated that images rated differently with respect to perceived activation and pleasantness elicited physiological responses of different magnitude. Thus, magnitude of the skin conductance response correlated with perceived arousal level produced by pictorial stimuli. At the same time heart rate acceleration during first 4 to 5 seconds of image presentation reflected "valence" or degree of perceived pleasantness of an image. Other physiological parameters that reflect an individual's physiological reactions to images have also been demonstrated. These results imply that, for an individual viewer, images can potentially be classified based on one's physiological reactions in terms of emotional arousal.

(2) Imagery is known to be able to change a person's state. Paintings, movies, pictures are constantly affecting our mood and performance level. Power of visualization and affective content determine effective use of imagery in therapeutic sessions. Experimental research has also shown that presentation of images of similar content may cause significant shifts in physiological reactions.

(3) Digital imaging technology provides an almost instant access to image databases through the internet. Moreover, the potentially unlimited degree of digital manipulation makes images very attractive means of interaction and communication. Images can be easily transformed to alter or enhance people's preferences, i.e., for hue, saturation, depth, aesthetic feelings, etc. Image transformation by itself can provide biofeedback information to the user to facilitate learning how to control one's physiological and emotional state, e.g., stress.

Following are several proposals to use images as a means of changing one's state that have not proven to be entirely successful.

U.S. Pat. No. 5,465,729, issued Nov. 14, 1995, inventors Bittman et al. and U.S. Pat. No. 5,343,871, issued Sep. 6, 1994, inventors Bittman et al., disclose the use of measurements of electrophysiological quantities to control a presentation to a subject of a series of prestored audio-visual sequences.

U.S. Pat. No. 3,855,998, issued Dec. 24, 1974, inventor Hidalgo-Briceno discloses an entertainment device that includes sensing means connected to the user for sensing galvanic skin response and brain theta waves. According to a given measured state of a user the device provides a given type of predetermined audio-visual stimulation to the user for a timed interval to hold one in or move one toward a desired state. At the end of the interval, the user's state is again measured and a further timed audio-visual response according to the measured state is presented to the user.

U.S. Pat. No. 5,596,994, issued Jan. 28, 1997, inventor Bro, discloses an automated and interactive positive motivation system that allows a health care professional to produce and send a series of motivational messages to a client to change or reinforce a specific behavioral pattern.

U.S. Pat. No. 5,304,112, issued Apr. 19, 1994, inventors Mrklas et al., discloses an integrated stress reduction system which detects the stress level of a subject and displays a light pattern reflecting the relationship between the subject's stress level and a target level. The system also provides relaxing visual, audio, tactile, environmental, and other effects to aid the subject in reducing one's stress level to the target level.

U.S. Pat. No. 4,632,126, issued Dec. 30, 1986, inventor Aguilar, discloses a biofeedback technique which permits simultaneous, preferably redundant, visual and auditory presentation on a color TV of any intrinsically motivating stimuli together with continuous information pertaining to the physiological parameter to be controlled. As the subject changes a certain physiological parameter, the image and sound become clearer if the change occurs in the desired direction.

U.S. Pat. No. 5,253,168, issued Oct. 12, 1993, inventor Berg, discloses a system for allowing an individual to express one's self in a creative manner by using biofeedback signals to direct imaging and audio devices.

U.S. Pat. No. 5,676,138, issued Oct. 14, 1997, inventor Zawalinski, discloses a multimedia computerized system for detecting emotional responses of human beings and changes thereof over time.

U.S. Pat. No. 5,047,930, issued Sep. 10, 1991, inventors Marten, et al., discloses methods of analyzing physiological signals from a subject and analyzing them using pattern recognition techniques to determine a particular sleep state of the subject. Use of any associated feedbacks is not disclosed.

The following papers discuss various emotional responses and physiological responses of subjects to viewing images.

Affective judgement and psychophysiological response: dimensional covariation in the evaluation of pictorial stimuli; by: Greenwald, Cook and Lang; Journal of Pyschophysiology 3 (1989), pages 51–64.

Remembering Pictures: Pleasure and Arousal in Memory, by: Bradley, Greenwald, Petry and Lang; Journal of Experimental Psychology, Learning Memory and Cognition; 1992, Vol. 18, No. 2, pages 379–390.

Looking at Pictures: Affective, facial, visceral, and behavioral reactions; by: Lang, Greenwald, Bradley, and Hamm, Psychophysiology, 30 (1993), pages 261–273.

Picture media and emotion: Effects of a sustained affective context; by: Bradley, Cuthbert, and Lang, Psychophysiology, 33 (1996), pages 662–670.

Emotional arousal and activation of the visual cortex: An fMRI analysis; by: Lang, Bradley, Fitzsimmons, Cuthbert, Scott, Bradley, Moulder, and Nangia; Psychophysiology, 25 (1998), pages 199–210.

The techniques disclosed in the above references have the following disadvantages.

1. There is no development of a personal image profile of an individual so as to provide for customized images which are specifically tailored for the individual so as to move the individual to a desired physiological and/or psychological state. This is important since an image which is restful for some may be stressful for others.

2. The images or other stimuli for inducing change in state in an individual are preselected by someone other than the user. The selection is often based on the effect of the images on a large number of subjects rather than being personalized for the individual.

3. Where measurement of physiological parameters are used as part of the state change technique, the measurement devices are often large and not very portable and therefore not conducive for use at work, at home or during travel.

SUMMARY OF THE INVENTION

According to the present invention there is provided a solution to the problems referred to above.

According to a feature of the present invention there is provided a method of managing a physiological or psychological state of an individual using images comprising: determining an individual's direction or preference for a state management session; based on the determination, deciding whether a current set of images selected through a personal image profile session, will achieve the desired management effect; if the current set are deemed satisfactory, presenting the set of images to the individual to achieve management of the individual's state.

ADVANTAGEOUS EFFECT OF THE INVENTION

The present invention has the following advantages.

1. An individual is profiled to provide customized images which are specifically tailored for the individual to move the individual to a desired physiological and/or psychological state.

2. The images or other stimuli for inducing change in the state of an individual arc not preselected by someone other than the user, but rather by the user.

3. A portable device is used to measure physiological parameters to predict an individual's state. The portable device is conducive for use at work, at home, during travel, or during exercise.

DETAILED DESCRIPTION OF THE INVENTION

General Discussion

Figure 14:
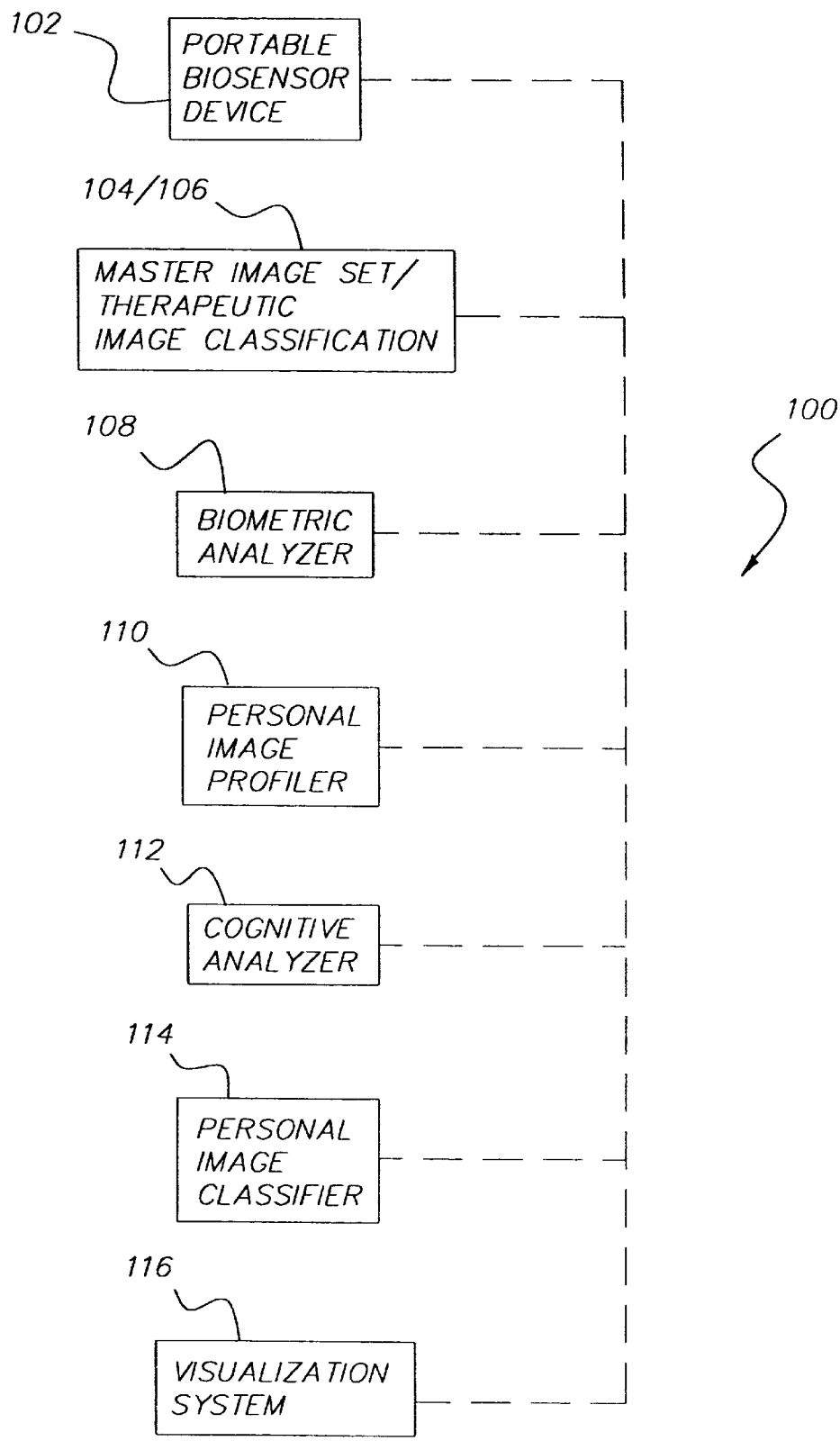
FIG. 14 is a block diagram of the system of the present invention.

In general, as shown in FIG. 14, the system 100 of the present invention includes several interrelated components that can be used to help one to manage one's physiological and or psychological state. These components will be described in greater detail later but, in general, include one or more of the following:

1. Portable Biosensor Device (102)

A portable biometric device that is worn or carried by a user and which senses and records physiological parameters on a continuous basis.

2. Master Set of Images (104)/Therapeutic Image Classification System (106)

A set of images presented to a user to determine the user's physiological and cognitive image preferences. The images are classified according to a therapeutic image classification system.

3. Biometric Analyzer (108)

A biometric analyzer which extracts the physiological activation state of user from one or more measured physiological parameters.

4. Cognitive Analyzer (110)

A cognitive analyzer which extracts cognitive state from cognitive responses to images.

5. Personal Image Profiler (112)

A personal profiler which combines the physiological and cognitive measures obtained from the biometric analyzer and cognitive analyzer to generate an individual's personal image profile for a given state response.

6. Personal Image Classifier (114)

A personal image classifier which, based on an image bank having images which have been classified using a therapeutic image classification system, and on the personal image profile, selects activating and deactivating images to create a personal image set.

7. Visualization System (116)

A visualization system which presents the personal image set to a person with the goal to help manage, modify or maintain current physiological and psychological state.

The components of system 100 can take different forms, depending on the application. For example, the portable biosensor device 102 measures one or more physiological parameters of an individual. The measurements can be recorded in the device and appropriate resident software used to analyze the state of the individual. Alternatively, the measured physiological parameters can be transmitted over a wireless channel to a server where they are recorded and analyzed. A warning signal can then be transmitted back to the portable device to warn the user of the need to manage one's state.

Components 104–112 can reside as software in a computer that is located with the individual, at a health care professional's office, or the like. The images selected by component 114 can reside in local or remote database(s) that can be communicated with over standard communication links (public telephone, cell phone, internet/world wide web, intranet, etc.). The visualization system 116, includes a display which can form part of a computer, a television, a handheld device, such as a PDA, game, or entertainment device, a slide projector, a cell phone. The visualization system can include devices such as a CD player, a DVD player, a VCR, etc. The system can include devices for other sensory feedback, such as, auditory, olfactory, tactile (heat, vibratory), etc. The applications of the present system are set out in greater detail below.

Figure 1:
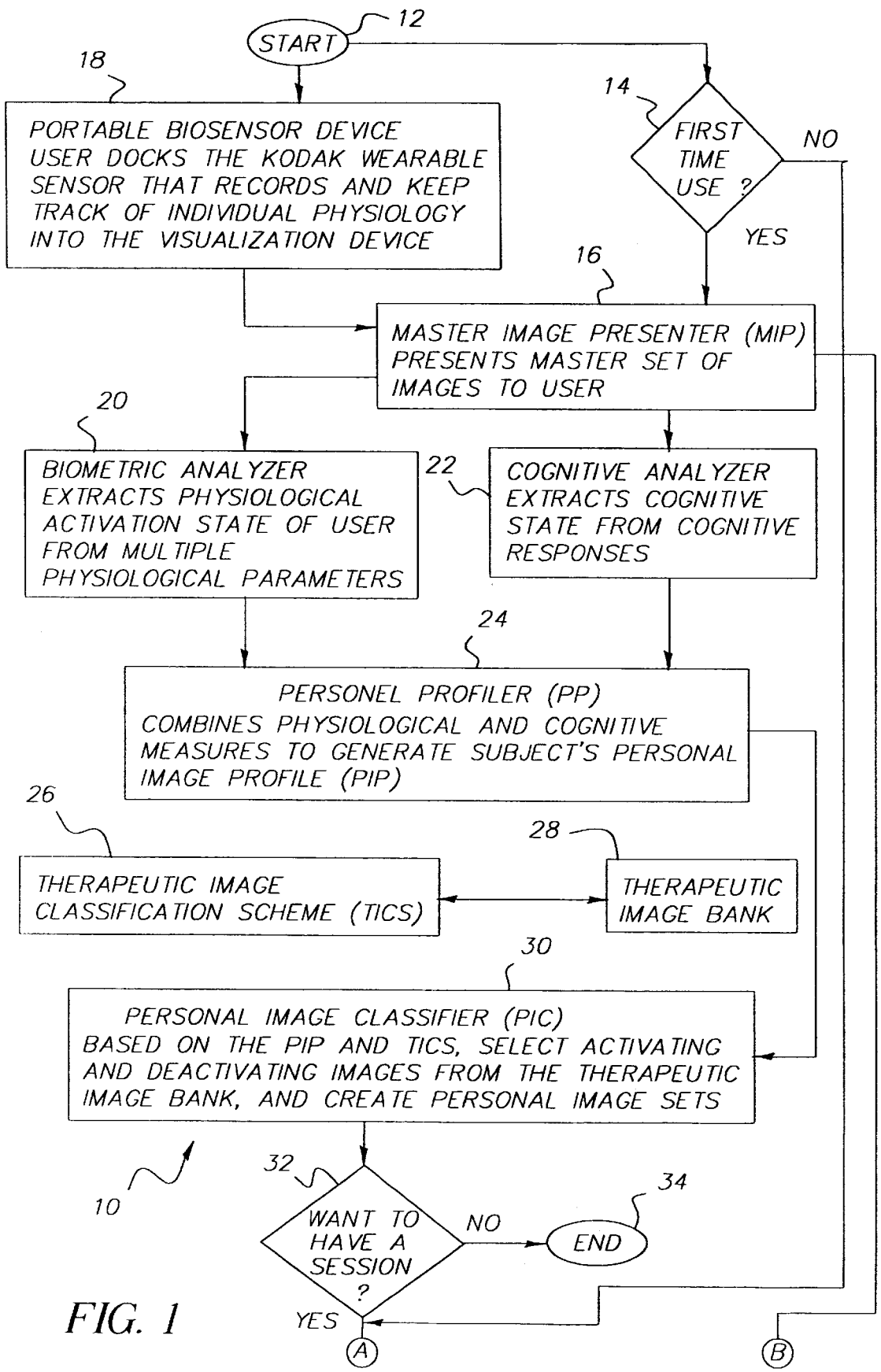
FIGS. 1 and 2 are flow diagrams useful in explaining the present invention.
Figure 2:
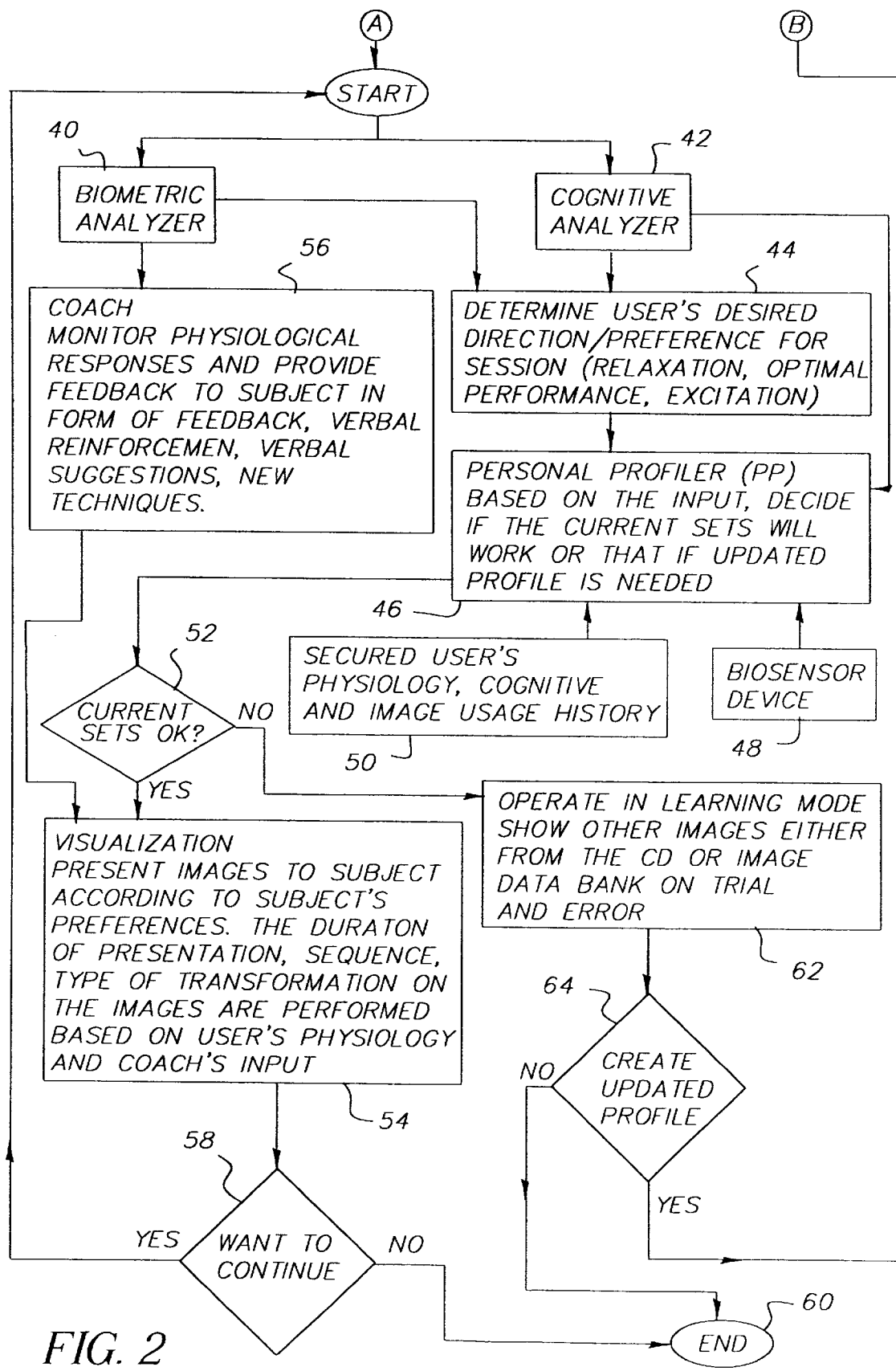

The interrelated use of these components is set forth in FIGS. 1 and 2. As shown in FIG. 1, the process 10 is started (bubble 12). It is determined (diamond 14) if this is a first time use. If the answer is no, the process of FIG. 2 is carried out (A). If the answer is yes, the process continues (box 16) where an appropriate visualization system presents a master set of images to the user. If the Portable Biosensor Device has been used, it is docked to the visualization device to give a record of physiological parameters of the user measured over a period of time (box 18).

The biometric analyzer(box 20) and cognitive analyzer measures (box 22) physiological and cognitive states from the user during presentation of the master set of images.

The personal profiler (box 24) generates the user's personal image profile based on the combined physiological and cognitive measures.

Based on the personal image profile and a therapeutic image classification system (box 26) for images in a therapeutic image data bank (databases) (box 28), activating and deactivating images are selected from the image data base(s) to create a personal image set (box 30).

The user then decides (diamond 32) if he or she wants to have a session. If no, the session ends (bubble 34). If yes, the process continues to A in FIG. 2.

Once a personal image set has been established, the user can start a session (A). The Biometric Analyzer (box 40) and Cognitive Analyzer (box 42) can be used to determine a user's desired direction/preference for a session (e.g., relaxation, optimal performance, excitation (box 44).

Based on the inputs, the Personal Profiler (box 46) decides if the current Personal Image set will work or if an updated, Personal Image profile is needed. The Personal Profiler can also receive inputs from a Portable Biosensor Device (box 48) and from a user's physiological, cognitive and image use history from a secured data base (box 50).

If the current image set is determined to be OK (diamond 52), the visualization device presents images to the user according to one's preferences. The duration and/or sequence of presentation, the type of transformation of the images are performed based on users physiology. (box 54) Input from a "Coach" (box 56) may also be provided. The "Coach" monitors physiological responses of the user and provides feedback in form of visual feedback, verbal reinforcement, verbal suggestions and new techniques.

The user then decides to continue or not (diamond 58). If yes, the process is returned to A. If no, the process is ended (bubble 60). If the current image set is determined to be not OK (diamond 52), the process is operated in a learning mode (box 62) where other images from an image bank are shown on a trial and error basis. The user may wish to create an updated profile (diamond 64). If "yes", the process continues to "B" in FIG. 1. If "no", the process is ended (bubble 60).

Following are more detailed descriptions of each of the components described above.

PORTABLE BIOSENSOR DEVICE

In medical compliance (taking medicine regularly, exercising regularly etc), it may be beneficial for a user to have a system that tracks, reminds, and rewards the user. On the same token, for an excellent individualized biofeedback based wellness management program, The Portable Biosensor Device tracks and reminds the user to perform wellness management as needed.

The Portable Biosensor Device is a portable device having one or more sensors that record physiological parameters of an individual wearing the device. Different individuals react differently to different sensors under different situations. Through individual sensor response profile (as explained in personal profiler section) we will be able to produce a personalized device. The device contains multiple sensors to measure temperature, heart rate variability (HRV) (measured either from ECG, photoplethysmographic methods or continuous blood pressure), SCR (skin conductance response), EEG, EMG, eye saccades etc.

Figure 3:
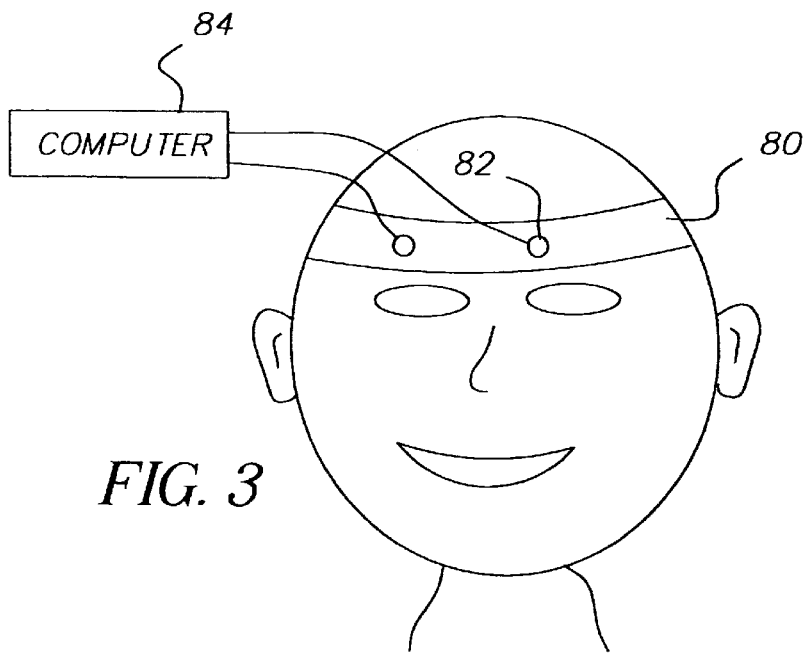
FIGS. 3–5 are diagrammatic views illustrating several embodiments of a portable physiological sensor monitor.
Figure 4:
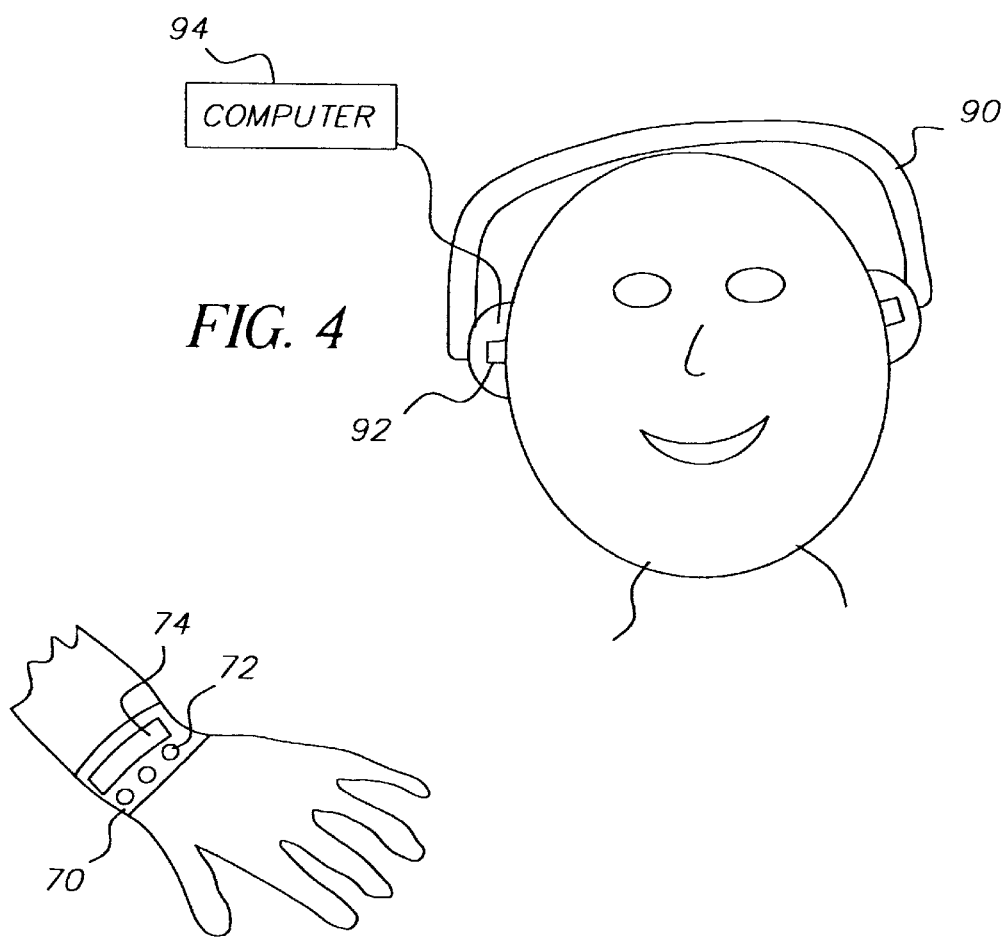
Figure 5:
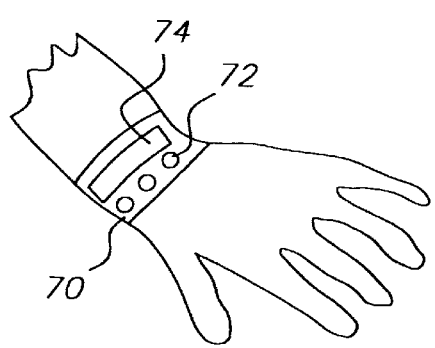

The device will accommodate different sensor sets based on the embodiment. For example as shown in FIG. 5, a wrist type device 70 with sensors 72 and computer 74 can record temperature, HRV through continuous blood pressure monitoring, and SCR. A head band type of device 80 with sensors, 82 connected to computer 84 (on waist band-not shown) shown in FIG. 3 can measure EEG and EMG. As shown in FIG. 4, an earphone type of device 90 with sensors 92 connected to computer 94 (on waistband not shown) could measure temperature, heart rate variability through photoplethysmographic methods, and SCR.

The portable biometric device is microprocessor based and records the user's physiology throughout the day, especially between sessions. Using digital signal processing on the sensor data, it will analyze (or analyze using the Profiler) and make predictions on the individual's state. Predictions will be made either using phasic physiological responses such as change in heart rate or SCR, or using sophisticated techniques such as Independent Component Analysis or pattern recognition. For example, increased heart rate and SCR could indicate activation or excitement, however, more sophisticated analysis could differentiate between excitement to startle and excitement in defense. According to Cacioppo et al (1996), though both the startle response and the defense response are associated with increased heart rate and SCR, they exhibit different patterns of activation. In the case of the startle response, the heart rate acceleration peaks and returns to near normal levels within two seconds, whereas in the case of the defense response, the heart acceleration does not begin to rise for several seconds and peaks much later.

Moreover, if the user chooses to know, the feedback to the individual user can be provided through either vibration (tactile or kinesthetic), auditory, or visual means. The data recorded in the device can either be stored on the device or transmitted to an individual server via wireless communication channel.

BIOMETRIC ANALYZER

The Biometric Analyzer plots, on a two/multi dimensional plot, physiological reactivity of each individual for different situations such as Baseline Different type of stressors (active coping task such as mental arithmetic, passive task such as situation narration)

Calmed state

Energized state

It should be noted that

1. The reactivity to specific images can also be plotted on this plot, and mapping is performed to cluster images in various groups.

2. Various sensor measures, such as EEG, EMG, HRU, eye saccades, hand temperatures, etc., can be simultaneously used.

3. Clustering of images into various groups can be done using techniques such as Euclidean distance, ratio of distances etc.

4. Plotting can be done using different techniques such as principal component analysis, or independent component analysis, wavelet, neural networks, time series, and other signal processing techniques.

One such technique (CLMOD) using principal component analysis, mapping images between a baseline and arithmetic stressor, using eye saccades, heart rate and EMG measures, and using a ratio of distance of the image to the stress to the distance of the image to the baseline is explained in more detail below. In general, this technique determines which images are physiologically "activating" or "deactivating". The technique can be implemented as follows.

A subject is seated in a comfortable chair before a display monitor. Sensors are attached to the subject to record biological information, such as, finger temperature, muscle tension, and heart rate. The physical responses are recorded while the subject views images presented on the monitor and while doing mildly stressful activities. The data is collected several (e.g., 256) times a second, while at rest, while viewing the images, and while cognitively rating them, as well as while talking about oneself and during a mental arithmetic task and during rest periods after each stress test.

A subset of the physiological measures from these time periods is selected for use. The data is prepared using Fourier analysis for some physiological measures and histograms for other physiological measures.

The data from the baseline, stress and rest time periods are broken into multiple, non-overlapping 15 second segments, and then a histogram or a spectrum computed from a Fourier analysis is used for each time segment. The histograms and/or spectra for each time segment are then fed into a Principal Component Analysis (PCA). In a preferred embodiment of this method, either Canonical Discriminant Analysis or Neural Networks might replace PCA. The result of the PCA analysis is that, (1) a set of weights called "loadings" is created, and (2) a set of "scores" or summary values, for each time segment is created. The data from the image periods are prepared using Fourier analysis and histograms, and the loadings are applied to these image period Fourier spectra and histograms. The result is a set of "scores" for each image period.

The image period scores are then compared to the scores for the baseline, stress and rest time segments. An image score that is "close" to the centroid of the baseline scores indicates an image that is "deactivating". An image that is close to the centroid of the stress scores indicates an image that is "activating". An image score that is not "close" to either the centroid of the baseline scores or the centroid of the stress scores indicates an image that is neutral. What is meant by "close" can be determined in several ways. One technique is to determine the Euclidian distance from each centroid and then create the ratio of the distance to baseline centroid divided by distance to stress centroid. The difference between the image score and the blank period score can also be used instead of the image score itself.

Following is a more detailed description of the CLMOD Analysis.

Description of Biometric Analysis

Figure 6:
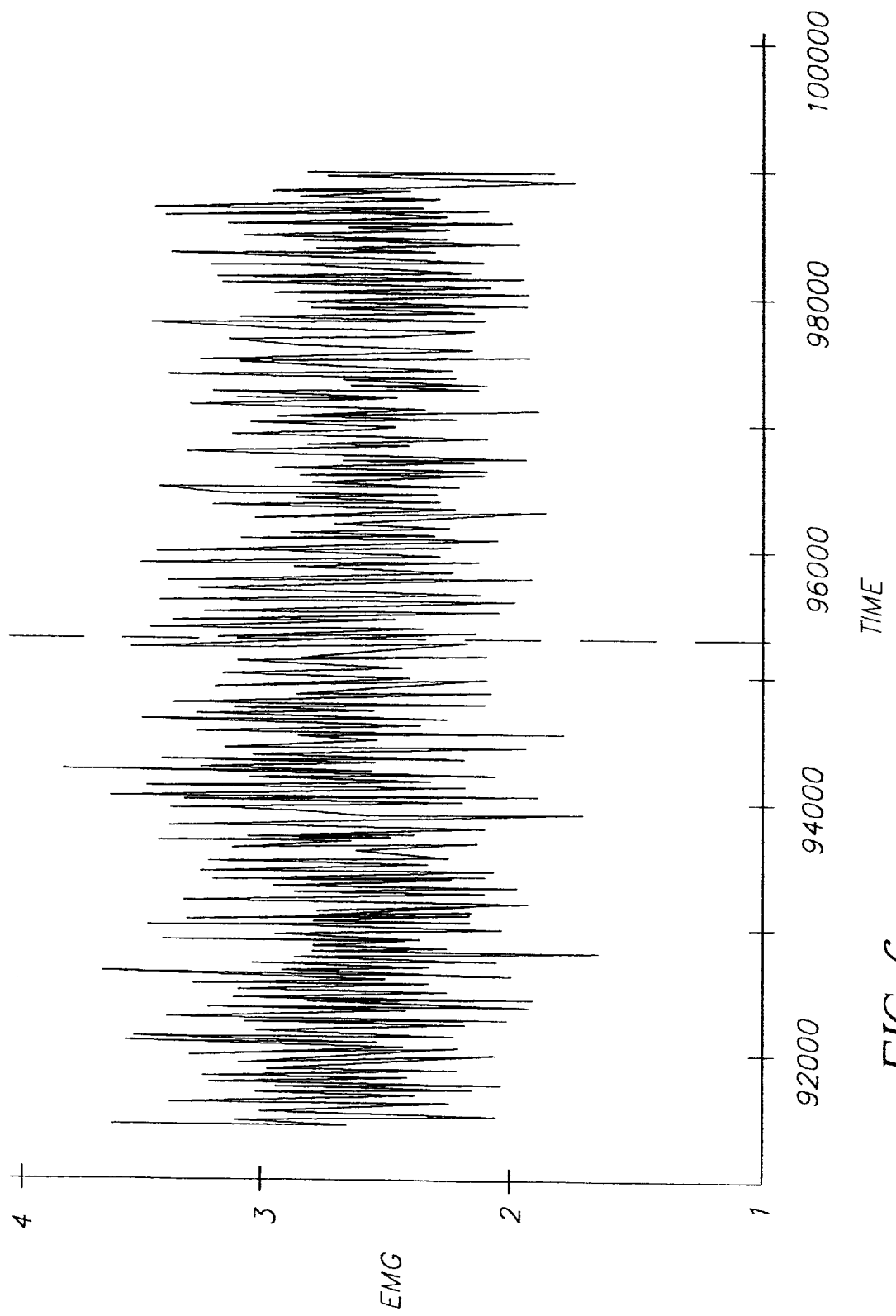
FIGS. 6–11 are graphical views useful in explaining certain aspects of the present invention.
Figure 7:
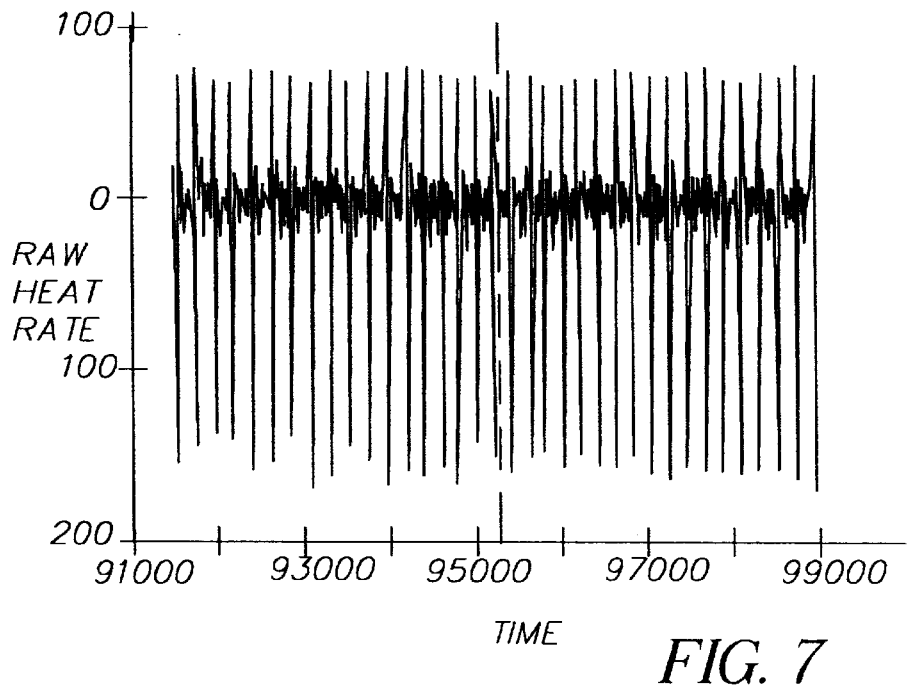

1. Take physiology for baseline, discard first 2 minutes and last 2 minutes and chop remainder into non-overlapping 15 second segments. Call the data in these segments $B_1$ through $B_{24}$. (An example of heart rate and EMG data for two consecutive 15 second segments are shown in FIGS. 6 and 7 respectively)

2. Take physiology for Stress 1, chop into non-overlapping 15 second segments. Call the data in these segments $S1_1$ through $S1_{12}$.

3. Take physiology for Stress 2, chop into non-overlapping 15 second segments. Call the data in these segments $S2_1$ through $S2_{12}$.

4. Take physiology for Rest 1, chop into non-overlapping 15 second segments. Call the data in these segments $R1_1$ through $R1_{12}$.

5. Take physiology for Rest 2, chop into non-overlapping 15 second segments. Call the data in these segments $R2_1$ through $R2_{12}$.

Figure 8:
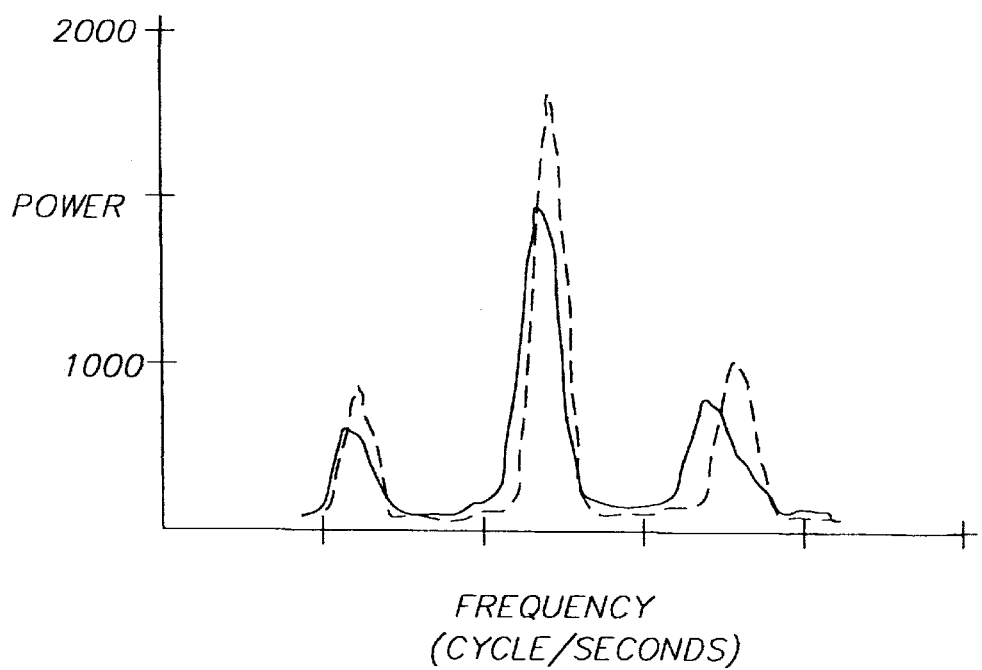

6. For each data segment $B_1$–$B_{24}$, $S1_1$–$S1_{12}$, $S2_1$–$S2_{12}$, $R1_1$–$R1_{12}$, $R2_1$–$R2_{12}$, perform the following calculations:

(a) Take the heart rate data and compute the periodogram (Fast Fourier Transform). Interpolate this periodogram so that the height of the periodogram is available at pre-specified intervals. An example of two periodograms that corresponds to the data shown in FIG. 7 is shown in FIG. 8.

Figure 9:
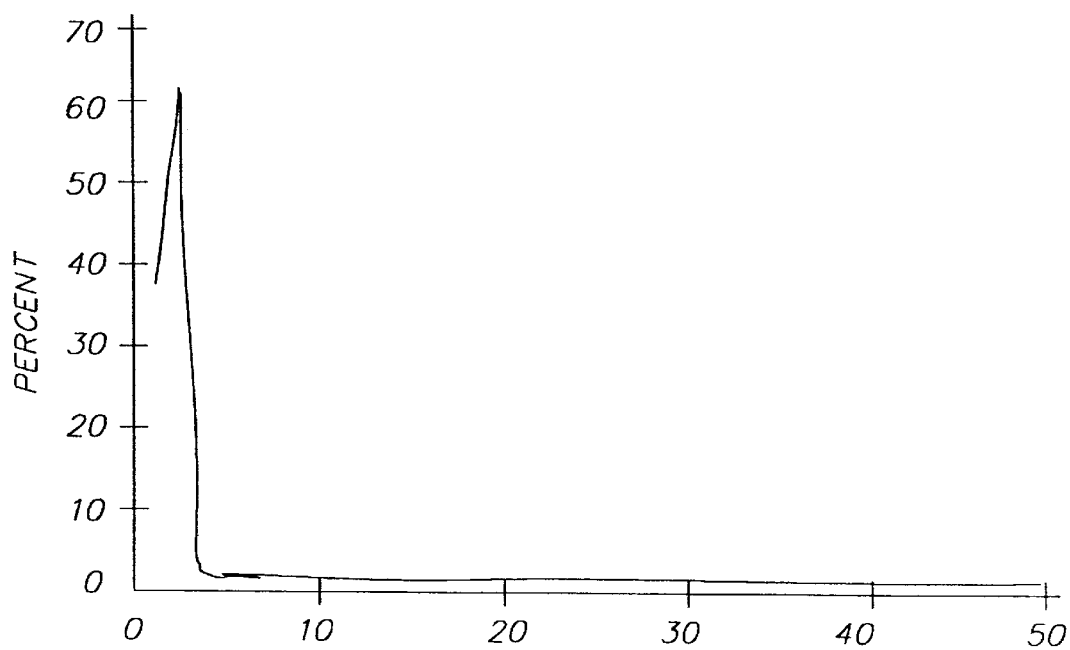

(b) Take the EMG data and compute the histogram, using pre-specified bin widths. Store the percent of data in each bin. An example of EMG histograms corresponding to the data shown in FIG. 6 is shown in FIG. 9.

7. Combine the heart rate interpolated periodogram, EMG histogram percents and Eye saccade histogram percents into one data set, where the rows are the different data segments and the columns are the histogram bins and/or periodogram heights. The histograms need to be aligned (and padded with zeros if necessary) so that the data in each column represents the same bin.

Figure 10:
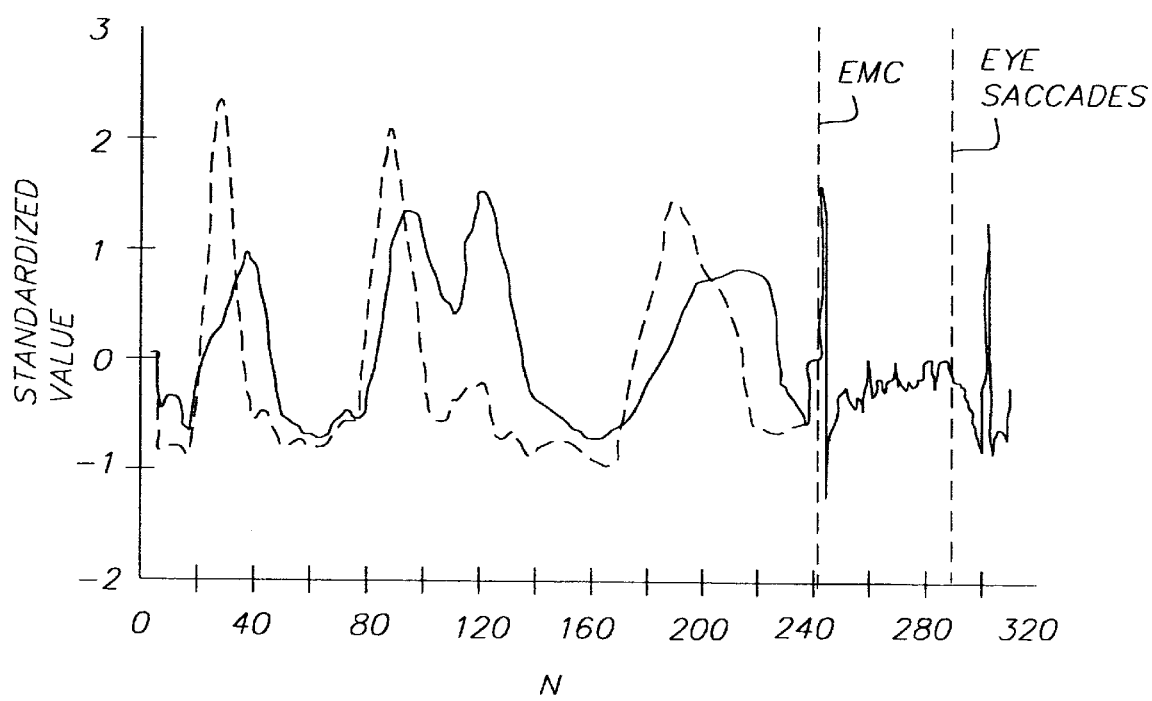

8. Scale this data set as follows: Subtract from each data point the mean of the column it is in. Each column then has a mean of zero. Each of the columns related to the heart rate interpolated periodogram has a variance (not standard deviation) of $1/n_H$, where $n_H$ is the number of pre-specified frequencies to use in the heart rate FFT. Each of the columns related to the EMG histograms has a variance of $1/n_{EMG}$, where $N_{EMG}$ is the number of such columns. Each of the columns related to the Eye Saccades histograms has a variance of $1/n_{EYE}$, where $n_{EYE}$ is the number of such columns. This scaling ensures that heart rate, EMG and Eye saccades contribute equally to the next analysis. An example of the result of this step is shown in FIG. 10, where the scaling has been performed not just for the two 15 second intervals shown on the plots, but across the entire set of 15-second segments as explained above.

9. Perform Principal Component Analysis (PCA) on this data, retaining the first 5 dimensions. (The number 5 was chosen arbitrarily, and it can vary from subject to subject.) Store the PCA scores in five dimensions.

10. For each image period, perform the analyses described above in 6a, 6b, 6c 7, and 8. In step 8, use the mean calculated in step 8, not a new mean calculated on the Image period data. Take care to align the columns of the histograms to match the way the columns are aligned for the baseline, stress and rest data. Call these data segments $I_1-I_{82}$. Apply the PCA vectors from step 9 to the $I_1-I_{82}$ data segments to compute PCA scores in five dimensions. Append these scores with the PCA vectors computed in step 9.

Figure 11:
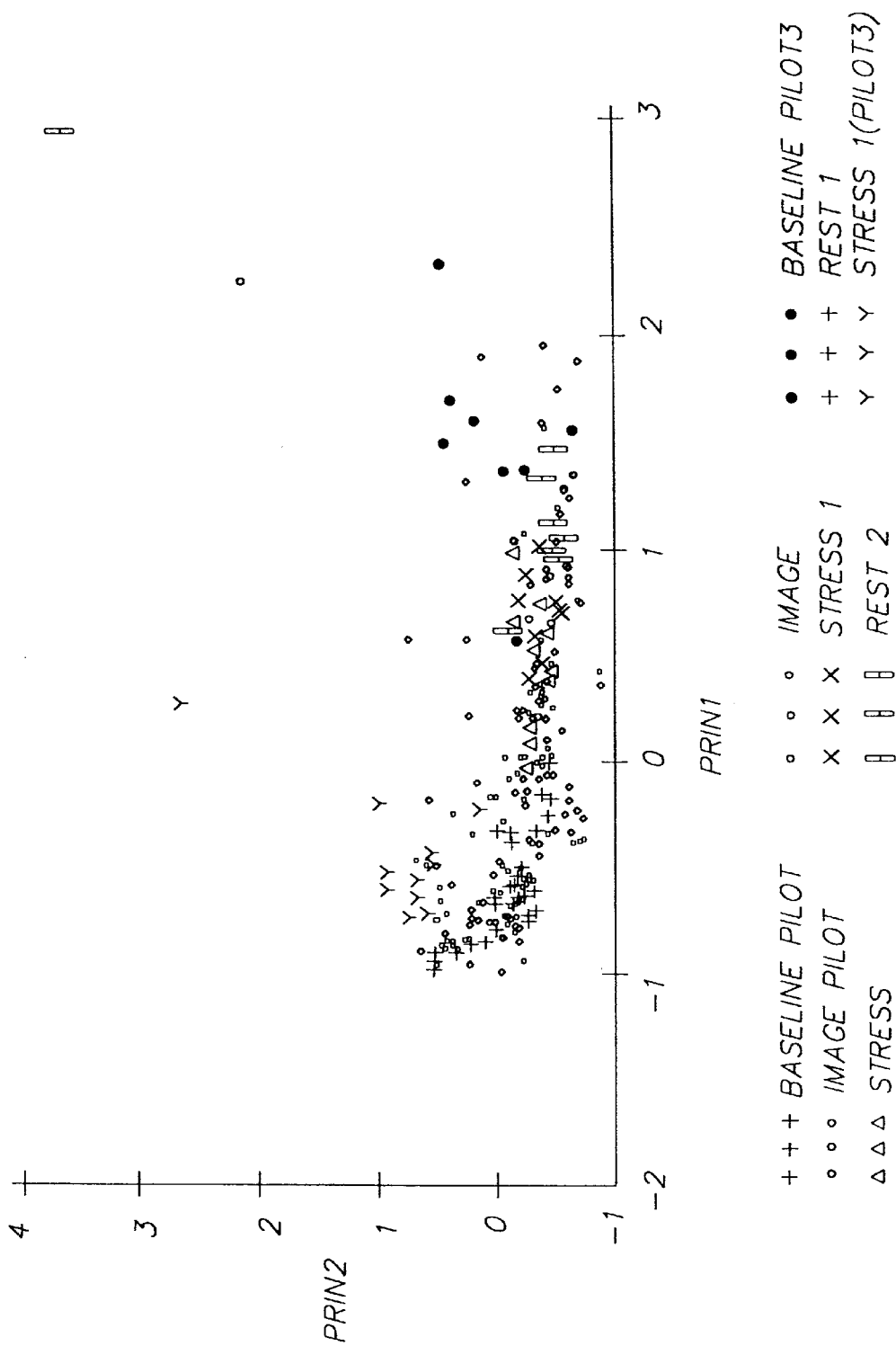
Figure 12:
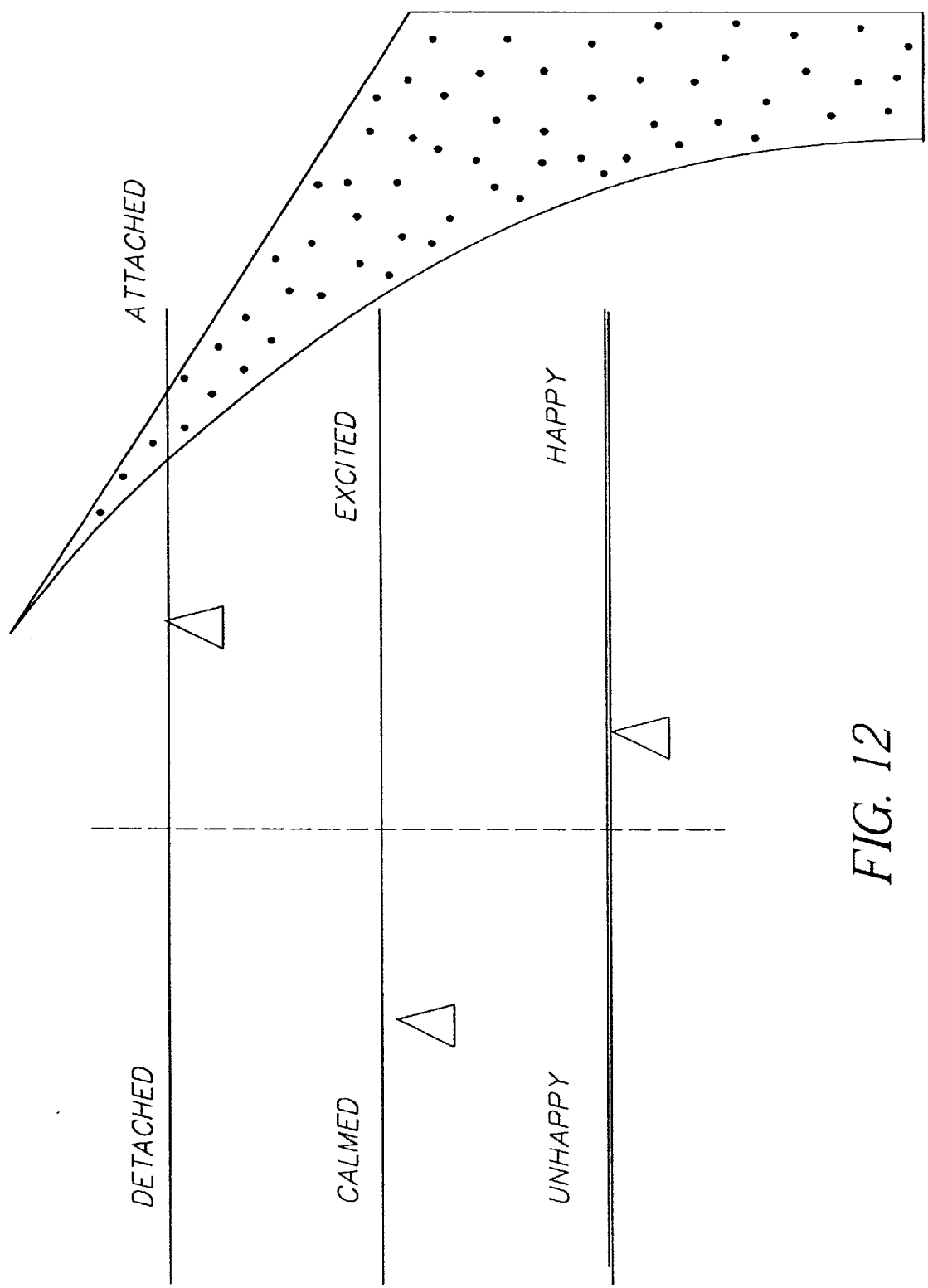
FIGS. 12 and 13 are diagrammatic views useful in explaining other aspects of the present invention.
Figure 13:
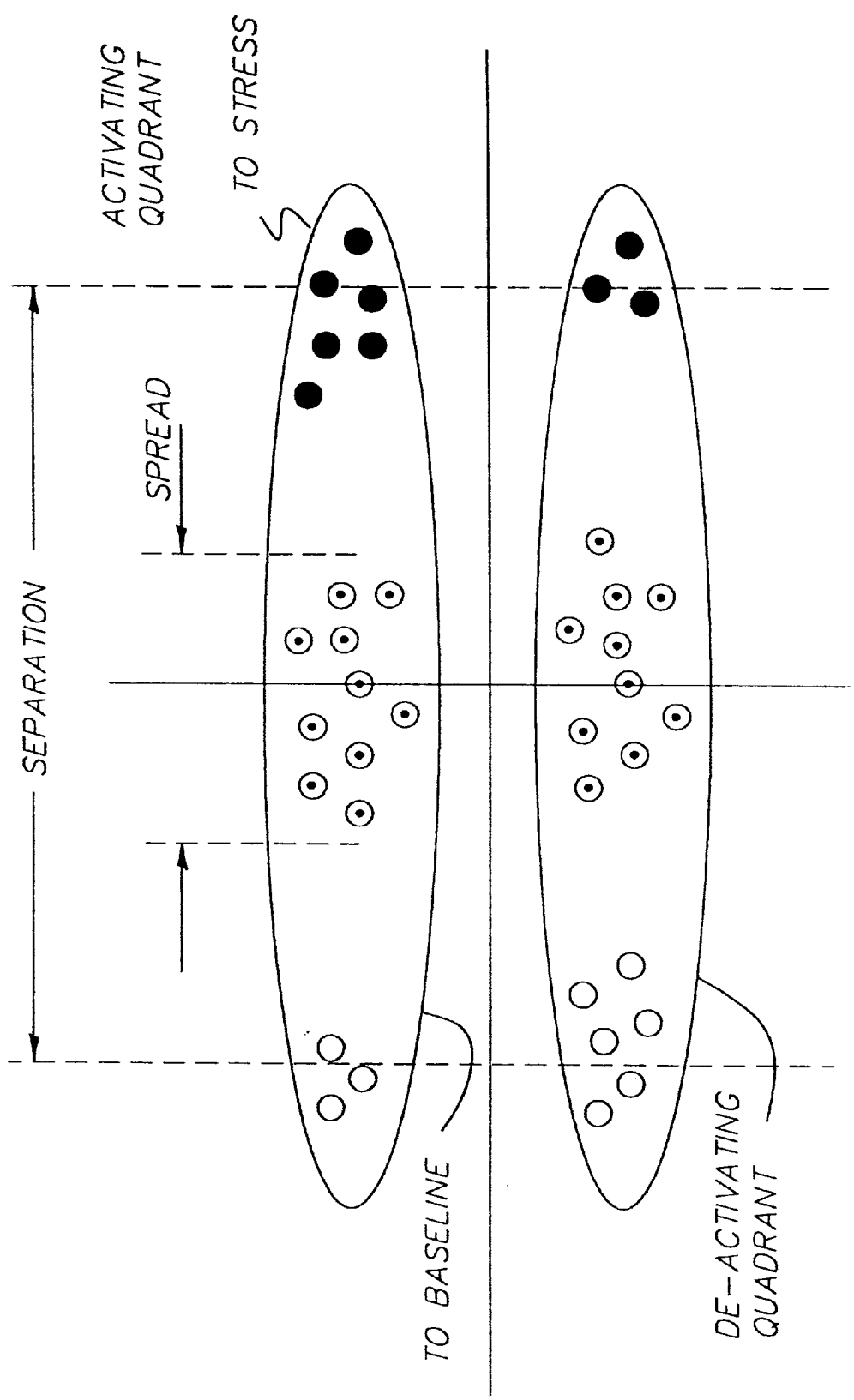

11. Plot the PCA scores in scatterplots, with different symbols for the different groups. An example of such a scatterplot is shown in FIG. 11.

12. Compute the distance in nd dimensions (where $n_d$ is some pre-specified number) of each image location in PCA space from the centroid (mean PCA score) of each of the baseline, stress and rest period data. The metric for activation and/or de-activation is any one or more of the following. A threshold or cutoff needs to be set to pick which images are activating or de-activating or neutral.

a). Distance from Baseline (or calmed state) Centroid b). Distance from Stress I (or activated state) Centroid c). Parks Ratio, which is (distance from baseline centroid)/(distance from stress 1 centroid)

Modified Biometric Analysis

10'. In addition to step 10 above, for each blank period perform steps 6a, 6b, 6c, 7, and 8. Call these segments $BL_1-BL_{82}$.

11'. In addition to step 11 above, apply the PCA vectors to data segments $BL_1-BL_{82}$.

11 . 5' Subtract the PCA scores for each image segment from the PCA scores from each blank period. Call these data $\Delta_1-\Delta_{82}$.

12'. Plot the PCA scores for $\Delta_1-\Delta_{82}$ instead of the PCA scores for the image periods $I_1-I_{82}$. Also, as in the previous step 12, plot the PCA scores for the baseline, stress and rest periods. The subtracted PCA scores are interpreted as showing the direction and amount of movement due to the change from blank to image period. Thus, we are really plotting the end of a vector whose other end is at the origin. An image that has vector length close to zero shows little physiological movement and can be interpreted as neutral.

The following steps are used to determine activation and deactivation:

(a) Determine the angle for each image $\Delta_1-\Delta_{82}$. This can be done in $n_d$ dimensions (where $n_d$ is some pre-specified number).

(b) Determine the set of angles for the baseline period data segments. If an angle for $\Delta_1-\Delta_{82}$ is contained in the range of angles for the baseline period and the length of the vector for each of $\Delta_1-\Delta_{82}$ is above some threshold, then we say that this image is de-activating. Vectors that point in the baseline direction but are less than this threshold value are considered neutral. (A modification would be to add ±k to the range of angles to allow for some uncertainty is our ability to locate the baseline cluster; k might be 10 degrees, we need to experiment to find a good value for k.)

(c) Determine the set of angles for the stress 1 period data segments. If an angle for $\Delta_1-\Delta_{82}$ is contained in the range of angles for the stress 1 period and the length of the vector for each of $\Delta_1-\Delta_{82}$ is above some threshold, then we say that this image is activating. Vectors that point in the stress 1 direction but are less than this threshold value are considered neutral. (A modification would be to add ±k to the range of angles to allow for some uncertainty is our ability to locate the baseline cluster; k might be 10 degrees, we need to experiment to find a good value for k.)

(d) Vectors that do not point towards either Stress 1 or Baseline are considered "other". These might be pointing towards other stress modes, or other calming modes, or they may be neutral. We cannot decide from this analysis.

Therapeutic Image Classification Scheme

This scheme is a set of a scene and image related features or attributes (or characteristics) that are relevant to potential therapeutic effect in a broad sense which includes emotional, sensational, cognitive, arousing, esthetical and any other possible impacts registered psychologically or psychophysiologically, that an image may produce while a person viewing the picture. By therapeutic effect, hence, we understand the ability of an image or series of images, video clips, or other visual material alone or in combinations with other modaltics purposely presented to improve a person's process, (quality, productivity or effectiveness) performance, state or attitude under consideration which otherwise would become a limiting or negative factor in the person's activities. These aspects are related to the person self, his/her interaction with the outside world (information, specific tasks, etc.) and inter-personal interaction and communication.

The above features are related to an appearance, content, composition, semantics, intentionally sought impression, uncertainty in interpretation, emotional load and probability of association with a particular emotion, etc. and ideally should represent all dimensions that may influence a holistic impression an image (or other type of visual and other stimulations mentioned above) produces.

The attributes can be rated in terms of importance and profoundness for each image.

THERAPEUTIC IMAGING CLASSIFICATION SCHEME

SUBJECT MATTER

Anything that appears to be a primary subject or part of the primary subject is categorized.

Defined categories include:

LANDSCAPES

Natural or imaginary scenery as seen in a broad view, consisting of one or more of the following elements which dominate a large percentage of and/or being central to the image.

Mountain

Water

Sun

Vegetation

Sand

Snow

Urban

PEOPLE—ACTIVITY

Static
  The subject either does not exhibit movement or intentionally poses.
Active
  Captured at the moment of active motion.
PEOPLE—EXPRESSION
  No Expression
Happy Faces
  A happy facial expression of a person that is the subject matter.
Unhappy Faces
  Unhappy facial expression of a person is a subject matter
PEOPLE
  Children
    People who appear to be 18 years old or younger.
  Family
    The primary subject includes a group of two or more people, regardless of age, exhibiting strong bonds of familiarity and/or intimacy.
ANIMALS
  Pets
    A domestic or tamed animal kept for pleasure or companionship (e.g., dogs, cats, horses, fish, birds, and hamsters).
    Pleasant
      A picture of a pet doesn't or is not intended to generate an unpleasant feeling or look.
    Unpleasant
      A picture of a pet does or is intended to generate an unpleasant feeling or look.
  Wild
    An undomesticated or untamed animal in its original natural state, or confined to a zoo or animal show (e.g., lions, elephants, seals, giraffes, zebras, and bears).
    Pleasant
      A picture of a wild animal doesn't or is not intended to generate an unpleasant feeling or look.
    Unpleasant
      A picture of a wild animal does or is intended to generate an unpleasant feeling or look.
ABSTRACT
  An image which achieves its effect by grouping shapes and colors in satisfying patterns rather than by the recognizable representation of physical reality.
OTHER
  Other can be used when neither of the defined categories of the subject matter can be applied.
LIGHTING
  Sun
    Predominantly distinct shadows are noted. This also includes indoor photos where the subject is directly illuminated by sun through a window. Shadows must be present. If the subject is shading itself, the primary type of light is SUN.
  Sunset/Morning/Evening
    This type of light is typified by long shadows.
  Hazy/cloudy/Overcast
    This type of light produces soft shadows (if any) and the light direction is often obscured, flat, and low contrast.
  Shade
    This light is relatively diminished or partial due to cover or shelter from the sun.
    This also includes Indoor pictures where the subject is illuminated by diffuse daylight from a window.
  Mix Sun and Shade
    This type of light includes spotty sunlight or a mixture of sun and shade.
  Flash
    A brief, intense burst of light from a flashbulb or an electronic flash unit, usually used where the lighting on the scene is inadequate for picture-taking.
COLOR/DOMINANT HUE
  Determined when one or two colors are seeing to be the prominent and global descriptors for a particular picture. If three colors are seen than we define that the picture does not have a dominant hue.
  Red
  Yellow/Orange
  Green
  Blue
  Purple/Magenta
  Brown
  White/Grey
  No Dominant hue (if more than 2)
DIRECTION OF LIGHT
  Front
    Light shining on the side of the subject facing the camera.
    Hints: Sunlight conditions where the shadow falls behind the subject. Flash pictures from point and shoot cameras.
  Side
    Light striking the subject from the side relative to the position of the camera; produces shadows and highlights to create modeling on the subject.
    Hints: Sunlight conditions where long shadow falls on the side of the subject.
  Back
    Light coming from behind the subject, toward the camera lens, so that the subject stands out vividly against the background. Sometimes produces a silhouette effect.
    Hints: TV's, Sunsets, and "Lights are Subject" are backlit. In backlit scenes, the shadow may fall in front of the subject, and appears to come towards the photographer.
  Zenith
    Light coming from directly above the subject.
    Hints: High noon lighting. Deep shadows in the eye sockets and below the chin.
  Diffuse
    Lighting that is low or moderate in contrast, such as an overcast day.
    Hints: Diffuse produces no shadows or just barely visible shadows, such as found on a cloudy, hazy day. Some mixed sun and shade pictures are also diffuse when the direction of light can not be determined.
  Multidirectional
    This indicates lighting coming from different directions, such as some stage lighting conditions or in a home where a window is on one side of the subject and a lamp on the other. Multiple shadows should be present if the lighting is from different directions and a flash was used.
TRAVEL/OFFSET DIRECTION OF GAZE MOTION/TRAVEL
  A subjective feeling (introspection) of moving one's eyes primarily along a particular trajectory or in a certain direction while viewing a picture.
  Centered
  Right to left/Left to right
  Up to down/down to up
  Multidirectional
  Distance
  Low 0–9 feet
  Medium 9–20
  High more than 20

COGNITIVE ANALYZER

Images from the master image set are presented to the subject to identify his or cognitive response profile in terms of which image attributes and images alter an individual emotional response and arousal level. The individual is asked to rank an image on one or more of three cognitive scales. Preferably, a measure of the cognitive preference computed from the scores along three cognitive scales is used, i.e., Valence, Arousal and Connectedness.

Definitions of Scales

Each scale is a two-ended scale with an anchor in the center marked 0. These three scales are described below:

Scale 1: Detached-Attached (Connectedness)

Detached   -4 -3 -2 -1 0 1 2 3 4   Attached

Detached is a feeling of not being able to personally connect or relate to the object or situation depicted in the image. Attached is a feeling of personnel connection to the object or situation depicted in the image.

Scale 2: Unhappy-Happy (Valence)

Unhappy   -4 -3 -2 -1 0 1 2 3 4   Happy

Unhappy is a feeling of sadness or disconnect that occurs when you view the object or situation depicted in the image. Happy is a feeling of contentment or satisfaction that occurs within you when you view the object or situation depicted in the image.

Scale 3: Calm-Excited (Arousal)

Calm   -4 -3 -2 -1 0 1 2 3 4   Excited

Calm is a feeling of tranquillity and silence that occurs within you when you view the object or situation depicted in the image. Excited is a physical state of being in which your feelings and emotions have become aroused that occurs when you view the object or situation being depicted in the image.

The user is given enough time to provide their reaction to each of the scales. He/she is instructed to follow their first impression. To facilitate the emergence of feelings that could be associated with an image, the users are encouraged to imagine themselves being "in an image" or part of an image that they are viewing. However, the users are requested not to force themselves to feel an emotion. Certain images may be neutral and elicit no emotions. Reactions will be different for each individual.

All three scales can be used individually to provide a measure of valence, arousal and connectedness. Each of them constitutes a valuable information source related to the person's reaction and can be independently used to assess them. The three scales can be combined to compute the measure of the cognitive preference.

Current implementation of the cognitive preference computation takes into account the absolute value of the total response, the variance of the ratings along each scale within an individual to normalize the response and logical rules that intend to increase the internal validity of the measure.

The method and procedure are as follows:

Step 1

Every image, I, is subjectively rated along each of the axes Attached/Detached (C), Calm/Excited (A) and Happy/Unhappy (V) such that it has three values C (I), A(I), and V (I) associated with it. $R(I_i) = \sqrt{(C^2(I_i) + A(I_i) + V^2(I_i))}$ Step 2

Normalize scale values $C(I_i) = C(I_i) * R(I_i) / \max_i R(I)$ $A(I_i) = A(I_i) * R(I_i) / \max_i R(I)$ $CI_i) = V(I_i) * R(I_i) / \max_i R(I)$ Where i=1 . . . , 82

Step 3.

Compute the standard deviation per scale:

$$S(V) = \sqrt{\frac{\sum_i (V(I_i) - \text{mean}(V(I_i)))^2}{n-1}}$$

$$S(A) = \sqrt{\frac{\sum_i (A(I_i) - \text{mean}(A(I_i)))^2}{n-1}}$$

$$S(C) = \sqrt{\frac{\sum_i (C(I_i) - \text{mean}(C(I_i)))^2}{n-1}}$$

Step 4.

Normalize every scale value from each image using appropriate standard deviations $C(I_i) = C(I_i)/S(C)$ $A(I_i) = A(I_i)/S\ C)$ $V(I_i) = V(I_i)/S(C)$ Step 5.

If $C(I_i) <= 1$, then $C(I_i)$ is Neutral along the C scale

If $A(I_i) <= 1$, then $A(I_i)$ is Neutral along the A scale

If $V(I_i) <= 1$, then $V(I_i)$ is Neutral along the V scale Step 6.

If image is Neutral along the V scale and is neutral along any other one scale it is overall neutral.

Step 7.

Paradoxical images

If image I is not neutral and (V(I)>0)&(C(I)<0)& (A(I)>0 or (V(I)<0)&(C(I)>0)& (A(I)<0 then

I is considered to be a paradoxical one.

Step 8.

Cognitively preferred.

If image I is not neutral and not paradoxical

I is cognitive preferred

<=>

(V(I)>0)

with the score equals V(I)

Step 9

Cognitively not preferred

If image I is not neutral and not paradoxical

I is cognitively not preferred

<=>

(V(I)<0) with the score equals V(I)

THE PERSONAL IMAGE PROFILER

Each individual user has their own characteristics; preferences of images, music, coaching etc., in other words, each person has a unique personal profile. This profile is thought to allow us to be better able to select images or other stimuli for the user. To be able to select images requires sophisticated methods not only to record but to analyze and understand the trait and state data of a person. The personal profiler does exactly that.

1. It gathers data from the portable biometric device (on going physiological data), biometric analyzer (Physiological data for different situations and images), and the cognitive analyzer (data on demographics, psychographics, cognitive preferences for images).

The preferred method is as follows:

Step 1. Selecting Activating/Deactivating images:
- a) Use BIOMETRIC analyzer method (e.g. CLMOD) to identify clearly activating or deactivating images. If the image is close to the baseline cluster then the image will be considered deactivating, or if the image is closer to the stressor cluster, then the image will be considered deactivating.
- b) Only in situations, where we do not have enough images to fill the four categories 1–4, we will use Calm/Exciting scale along with the BIOMETRIC analyzer method to pick activating/deactivating images.
- c) Ranking rule: The images will be ranked based on following criteria a. Ratio of distance of the image to stressor and baseline Step 2. Dividing the Activating/Deactivating images into C+ and C− categories:
- a) Use data from the scales in COGNITIVE ANALYZER to categorize images as preferred or not preferred. We do not use Calm/Excited scale.
- b) For PARADOXICAL images make decisions using rules specified in the COGNITIVE ANALYZER:
- c) Ranking rule: The Euclidean distance on Unhappy/Happy and Detached/Attached scales will be used to rank the images in the C+ and C− categories. The top ranking images will be used if the total number of images in each category is more than 10.

Step 3. Augment images by reducing threshold if necessary
- a) If the number of images in any of the four categories (picked based on Biometric analyzer method, and cognitive scales) is less than 4 then we will try to
  Increase the number of images by lowering the threshold in BIOMETRIC model
  Increase the number of images by lowering the threshold in the cognitive model to 0.55 SD (currently the threshold is 0.67 SD)
- b) If the number of images in any category are more than 4 but less than 10, we will try to maximize the number of total images using upto 5 similar for each image. The minimum number of images in each session would be 15 and maximum will be 20.
- c) If the number of images from any category are more than 10, we will pick the top 10. The ranking will be based on ranking rules specified in steps 1 and 2. The total number of images will be 30 and we will pick upto 2 similar for each image.

Step 4. Handle images that show very high physiology but neutral cognitive
- a) We reduce the threshold of the two cognitive scales to to 0.55 SD to see if that puts the image in consideration into C+ or C−.
- b) If not, we assign the image into both the C+ and C− category Step 5. Handle images that show very high cognitive but neutral physiology
- a) We reduce the threshold in BIOMETRIC ANALYZER model to see if that puts the image in consideration into activating or deactivating.
- b) If not, we assign the image into both the activating and deactivating category 2. Based on this data, it creates an individualized profile. The profiler uses generic models and population data to make predictions and personalization of coaching, stimuli, and even the user interface of the image presentation device.

3. Using digital signal processing on the sensor data, it analyzes and makes predictions on the individual's state. Predictions will be made either using phasic physiological responses, such as change in heart rate or SCR, or using sophisticated techniques, such as individual component analysis or pattern recognition. For example, increased heart rate and SCR could indicate activation or excitement, however more sophisticated analysis could differentiate between startle and defense. According to Cacioppo et al (1996), although startle response and defense response are both associated with increased heart rate and increased SCR, they exhibit different patterns of activation. In the case of startle, the heart rate acceleration peaks and returns to near normal levels within two seconds, whereas in the case of defense response the heart acceleration does not begin to rise for several seconds and peaks much later.

4. All the data is recorded in the profiler for future reference and use. The Personal Profiler also keeps records of data collected from subsequent biofeedback sessions.

5. Using statistical methods, the profiler tries to understand what worked and what did not.

PERSONAL IMAGE CLASSIFIER

The Personal Profiler collects the data from the BIOMETRIC analyzer and COGNITIVE analyzer and classifies the images into 1) Cognitively preferred/Physiological activating
2) Cognitively preferred/Physiologically deactivating
3) Cognitively not preferred/Physiological activating
4) Cognitively not preferred/Physiological deactivating Images selected using cognitive analyzer and biometric analyzer are treated as a collection of images that describes an individual image profile. After classifying the master images into these four categories, the Personal Image Classifier, builds these image sets by picking images from the Therapeutic Image Bank using similarity metrics method. Therapeutic image bank uses the therapeutic image classification scheme to accurately mark each individual image with its inherent characteristics. The goal is to find images similar to each image in a profile to create sets of images that share similar characteristics with respect to individual's reactions. Therapeutic image bank may contain personal pictures as well as stock photographs. The ultimate goal is to be able to classify images automatically using this scheme. The procedure currently used is:

1. All the images in the image bank are tagged with a 0 (for a particular feature not existent in the image) or 1 (for a particular feature not existent in the image), as shown in tables below. The columns represent the features from the classification scheme.

| # | ABS | OTH | LANDSCAPE | | | | | | | ACT | | PEOPLE/ EXPRESSION | | | PEOPLE | |
|---|-----|-----|----|----|----|-----|-----|-----|-----|-----|-----|-----|-----|-----|-----|-----|
| | | | Mt | Wt | Vg | Sun | Snd | Snw | Urb | Sta | Act | Non | Hap | Unh | Chd | Fam |
| 1 | 0 | 1 | 0 | 0 | 0 | 0 | 0 | 0 | 0 | 0 | 1 | 0 | 0 | 0 | 0 | 0 |
| 2 | | 1 | | | | | | | | 1 | | | | | | |
| ... | | | | 1 | | | | | | | 1 | | | | | |
| N | | | | | | | | | | | 1 | | | | | |

| | ANIMALS | | | | | | | | | LIGHT DIRECTION | | | | | |
|---|----|----|----|----|----|-----|-----|-----|-----|-----|-----|-----|-----|-----|-----|
| | Pleasant | | Unplesnt | | LIGHTING | | | | | | | | | | |
| # | Pet | Wld | Pet | Wld | Sun | Snst | Haz | Othr | Ind | Fmt | Side | Bac | Znith | Dfus | |
| 1 | 0 | 0 | 0 | 0 | 0 | 0 | 0 | 1 | 0 | 0 | 0 | 1 | 0 | 0 | |
| 2 | | | | | | | | | | 1 | | | | | |
| ... | | | | | | 1 | | | | | | | 1 | | |
| N | | | | | | | | | 1 | | 1 | | | | |

| | COLOR — DOMINANT HUE | | | | | | | | DISTANCE | | | TRAVEL/OFFSET | | | |
|---|-----|------|----|-----|-----|-----|-----|-----|-----|-----|-----|-----|-----|-----|-----|
| # | Red | Y/Or | Grn | Blu | Prp | Bm | Gry | Blk | Non | Low | Medm | Hig | Ctr | U/D | L/R | Mult |
| 1 | 0 | 1 | 0 | 0 | 0 | 0 | 0 | 0 | 0 | 0 | 1 | 0 | 0 | 1 | 0 | 0 |
| 2 | | 1 | | | | | 1 | | | 1 | | | | | | 1 |
| ... | | | 1 | | | 1 | | | | | 1 | | 1 | | | |
| N | | | | | | 1 | | | | 1 | | | | 1 | | |

2. To build a particular image cluster (say calming images), copy the classification record of all calming images from the master set for the particular individual into a buffer.

3. Examine each image from this buffer and using similarity matrix techniques such as Minkowski method, find similar images from the image bank. A similarity metrics can be established as the sum of all agreements between image features established in the step 1 and weighted by the feature importance (for an individual). Thus the Minkowski metric with various exponents can be used to determine the similarity. We used the value of the exponent equal to 1. Weighting coefficients are determined experimentally using a screening or specifically designed testing procedure and are considered as the order of an individual's feature importance related to the therapeutic effect.

4. Copy the new formed cluster into a new database for the individual with other metadata such as user identification, data and time of clustering, physiological reactivity to each image, cognitive reactions to each image.

This metadata will eventually be used in the personal profiler to evaluate the effectiveness of images in subsequent sessions.

VISUALIZATION SYSTEM

This is the main component that the user works with images to relax, energize, or do biofeedback training. This could be implemented on a computer, TV with set top box, handheld device such as PDA's, CyberFrames, or gaming devices. The purpose of the Visualization System is to allow participants to maintain their mind-body wellness using proper personalized coaching based on trends in physiology and cognitive feeling. Uniqueness of Visualization System is:

Personalized image selection and training that understands the users trends in activation or deactivation.

Coaching that continues even after the session and allows one to do a retrospective analysis of physiology changes between sessions.

Intelligent image understanding and personal preference data allows the coach to guide the user to certain parts of image or to a totally different image as needed.

The overall mind-body wellness is achieved by presenting a series of stimuli (e.g. images) that are selected based on personal cognitive and physiological preferences in an order that is "natural" for the individual, along with personalized coaching and relevant feedback. The process includes the following steps:

(1) To initiate a session, the user docks the buddy into a docking station (if the image presenter is implemented on a TV or a desktop computer) or into a docking port if it is a handheld device.

(2) If this is the first session, the system needs some profiling data to understand what images are suitable for this individual. The profiling is done using a Master Image Presenter and Personal Profiler. The system records demographics and psychographics data for the user.

(3) A master set of images (A Kodak set designed based specifically for different cultures) are presented to the user and their cognitive feelings and physiological reactivity are recorded for each image.

(4) As described in the Personal Profiler (including biometric analyzer and cognitive analyzer), the cognitive preference is recorded using the three scales, whereas physiological reactivity is recorded for the most sensitive measures. The physiological sensitivity for each individual is recorded using different situations such as baseline, different stress activities, calming, and energizing activities.

(5) As described in the Personal Image Classifier, the cognitive and physiological feelings are combined using certain rules and used to categorize the master set images into preferred calming, preferred activating, and neutral images. The Personal Image Classifier builds a unique set of images for the individual, based on similar images selected from the therapeutic image classification scheme and the therapeutic image data bank. Each image is coded with metadata, such as the features of the image, its rank on physiological reactivity for the subject, its rank on the cognitive scaling, etc. This metadata is used eventually to decide when and how long this particular image will be presented. At this stage either cognitive, physiology or both can be used for categorization. Different product embodiments can have different implementations.

(6) In subsequent sessions, the Image Presentation Device uses the unique image set in presentation.

(7) Establish the identification of the participant before allowing access to the system either through password authentication or physiology measures signatures. Understand from the user what they would like to do today and try to assess the correlation between how they feel cognitively and what their physiology is suggesting.

(8) Provide general instructions on how to breathe as the user views different images. This coaching will be a combination of diaphragmatic breathing, autogenics, guided imagery, and meditation thoughts. The Visualization System incorporates appropriate coaching (male/female voice, autogenics/no autogenics, some mechanism of trust-building, diaphragmatic breathing etc), different types of feedback, personalized order of presentation, personalized schemes of fading, and appropriate timing.

(9) Feedback can be either direct feedback through either digital readouts of physiology and/or various graphical means such as abstract bars, trend charts, slider graphs, colored bar graphs, etc., or indirect feedback through changes in the image parameters such as hue, saturation, sharpness.

(10) The system will also provide continual reinforcement based on the trend and temporal changes in the user's physiology state.

(11) Through out the session, the system tracks the physiology trends on the sensors that are most sensitive to the user. The intelligent coaching agent has certain generic rules built in. It also has a learning system that understands and records the user's sensitivities to different physiology measures as well as their responsiveness, and according modifies the instructions. The coaching agent bases its instruction both on the physiological changes as well as the feelings that are recorded through cognitive scales.

(12) The user interacts with the coach through natural interactions such as speech, direct point and click, and physiology changes. The coaching agent has a "persona" that is customized for each individual. Different persona of the coach could be varied on the gender, ages, instruction styles, mannerisms, personality types that a particular user likes. Certain amount of anthropomorphism is also provided in the coaching agent to facilitate one-to-one connection between the coach and the user.

(13) The coach also has intelligent image understanding and provides certain cues on contents of the images. These cues are stressed if the coach has prior knowledge about the user's preference.

(14) Apart from the individually selected mix of images, the Visualization System also provides individual image categories (sunset, beaches, rain, landscapes, family, children etc).

(15) It also provides both individualized and generic transforming images. Transforming images can include images that transform existing content such as an image showing sunset, or a flower blooming as well as adding new content e.g. a waterfall scene with a rainbow added to the scene if the user achieves a certain stage in the calming process.

(16) Throughout the session the Personal Profiler records the efficiency of the images. The profiler keeps record of what worked and what did not. (This is thought at the current moment to be available in the advanced implementation).

(17) The influence of the Visualization System on the user's behavior does not end at the end of the session. At the end of the session, the coaching system records how the user feels and will tell the user that they should carry the feelings and learning from this session to the real world. The user physiology will be monitored by the portable biosensor device between the sessions. The coach can then query, understand and advise the user based on the physiology data that is collected between sessions.

The invention has been described in detail with particular reference to certain preferred embodiments thereof, but it will be understood that variations and modifications can be effected within the spirit and scope of the invention.

PARTS LIST 10 process
12 60 process steps
70 wrist type device
72 sensors
74 computer
80 head band type device
82 sensors
84 computer
90 earphone type device
92 sensors
94 computer
100 system
102 portable biosensor device
104 master set of images
106 therapeutic image classification system
108 biometric analyzer
110 cognitive analyzer
112 personal image profiler
114 personal image classifier
116 visualization system

What is claimed is:

1. A method of managing a physiological or psychological state of an individual using images comprising:

determining an individual's direction or preference for a state management session;

based on the determination, deciding whether a current set of images selected through a personal image profile session, will achieve the desired management effect; and if the current set is not deemed satisfactory, creating a new set of images based on a personal image profile session wherein a master set of images classified according to a therapeutic imaging classification system, are presented to the individual, and using biometric and cognitive analysis of the presented images, generating a new personal image profile which is used to create said new set of images from an image database.

2. The method of claim 1 wherein said determining step is effected by personal choice of the individual.

3. The method of claim 1 wherein said determining step is effected by the measurement of selected physiological parameters of the individual.

4. The method of claim 3 wherein said physiological parameters are measured by means of sensors carried by the individual in a portable biometric device.

5. The method of claim 3 wherein said measured physiological parameters include one or more of, EMG, EEG, heart rate, blood pressure, skin conductance response, skin temperature, eye saccades.

* * * * *